(12) United States Patent
Odell et al.

(10) Patent No.: US 7,504,531 B2
(45) Date of Patent: Mar. 17, 2009

(54) PROCESSES FOR PREPARING DIFUNCTIONAL COMPOUNDS

(75) Inventors: Peter G. Odell, Mississauga (CA); Rina Carlini, Mississauga (CA); Lu Jiang, Oakville (CA)

(73) Assignee: Xerox Corporation, Norwalk, CT (US)

( * ) Notice: Subject to any disclaimer, the term of this patent is extended or adjusted under 35 U.S.C. 154(b) by 275 days.

(21) Appl. No.: 11/451,373

(22) Filed: Jun. 13, 2006

(65) Prior Publication Data

US 2007/0255038 A1 Nov. 1, 2007

Related U.S. Application Data

(60) Provisional application No. 60/745,921, filed on Apr. 28, 2006.

(51) Int. Cl.
C07C 69/00 (2006.01)
C08G 69/08 (2006.01)

(52) U.S. Cl. .................................. 560/129; 528/310

(58) Field of Classification Search .................. 560/129
See application file for complete search history.

(56) References Cited

U.S. PATENT DOCUMENTS 4,045,416 A * 8/1977 Robson et al. .............. 528/392
2006/0159850 A1 * 7/2006 Breton et al. .............. 427/258

FOREIGN PATENT DOCUMENTS

JP 63099038 A * 4/1988
JP 07010795 A * 1/1995

OTHER PUBLICATIONS

Song et al.; *Shiyou Daxue Xeebao, Ziran Kexueban*, vol. 24, No. 6; pp. 49-51; 2000.
Liu et al.; "Synthesis and Properties of Functional Aliphatic Polycarbonates;" *Journal of Polymer Science: Part A: Polymer Chemistry*; vol. 41; pp. 4001-4006; 2003.
Li et al.; "Synthesis, Characterization, and Thermal Behavior of H-Shaped Copolymers Prepared by Atom Transfer Radical Polymerization;" *Macromolecules*; vol. 37; pp. 5190-5195; 2004.
Ihre et al.; "Fast and Convenient Divergent Synthesis of Aliphatic Ester Dendrimers by Anhydride Coupling;" *J. Am. Chem. Soc.*; vol. 123; pp. 5908-5917; 2001.
Lu et al.; "Preparation and properties of starch thermoplastics modified with waterborne polyurethane from renewable resources;" *Polymer*; vol. 46; pp. 9863-9870; 2005.
Guan et al.; "Synthesis of Biodegradable Poly(ester amide)s Containing Functional Groups;" *Journal of Polymer Science*; vol. 43; pp. 1144-1149; 2005.
U.S. Appl. No. 11/289,609, filed Nov. 30, 2005, to Peter G. Odell et al.
U.S. Appl. No. 11/289,573, filed Nov. 30, 2005, to Gregory J. Kovacs et al.
U.S. Appl. No. 11/289,605, filed Nov. 30, 2005, to Gregory J. Kovacs et al.
U.S. Appl. No. 11/289,521, filed Nov. 30, 2005, to Jennifer L. Belelie et al.
U.S. Appl. No. 11/289,615, filed Nov. 30, 2005, to Jennifer L. Belelie et al.
U.S. Appl. No. 11/289,552, filed Nov. 30, 2005, to Jennifer L. Belelie et al.
U.S. Appl. No. 11/289,620, filed Nov. 30, 2005, to Peter G. Odell et al.
U.S. Appl. No. 11/289,375, filed Nov. 30, 2005, to Daryl W. Vanbesien et al.
U.S. Appl. No. 11/289,473, filed Nov. 30, 2005, to Rina Carlini et al.
U.S. Appl. No. 11/136,525, filed May 25, 2005, to Jennifer L. Belelie et al.
U.S. Appl. No. 11/451,342, entitled "Vehicles for Ink Compositions," filed concurrently with the instant application, to Peter G. Odell et al.
Co-pending U.S. Appl. No. 11/034,850, filed Jan. 14, 2005, to Peter G. Odell et al.
Co-pending U.S. Appl. No. 11/034,856, filed Jan. 14, 2005, to Peter G. Odell et al.
Co-pending U.S. Appl. No. 11/034,714, filed Jan. 14, 2005, to Jennifer L. Belelie et al.
Co-pending U.S. Appl. No. 11/018,378, filed Dec. 22, 2004, to Peter G. Odell et al.
Co-pending U.S. Appl. No. 11/034,866, filed Jan. 14, 2005, to Marcel P. Breton et al.

* cited by examiner

*Primary Examiner*—Sikarl A Witherspoon
(74) *Attorney, Agent, or Firm*—Oliff & Berridge, PLC

(57) ABSTRACT

Processes for preparing diacryl-functional compounds are provided. Processes include reacting $AB_2$ monomers with acryloyl halides, and then further reacting with long-chain, mono-functional aliphatic compounds to form long-chain diacrylates. Further processes include reacting difunctional tic compounds with acrylic acid to form difunctional diacrylate, and diacrylamide compounds.

21 Claims, No Drawings

PROCESSES FOR PREPARING DIFUNCTIONAL COMPOUNDS

This application claims the benefit of U.S. Provisional Application No. 60/745,921 filed Apr. 28, 2006.

TECHNICAL FIELD

This disclosure relates generally to processes for the synthesis of difunctional compounds, and to the use of such difunctional compounds in ink-jettable ink compositions. In particular, this disclosure provides methods for producing difunctional ester compounds having long hydrocarbon chains by reacting difunctional carboxylic acids with acyloyl halides, and condensing the reaction products with long-chain alcohols. This disclosure also provides methods for producing diacryl-functional compounds by reacting difunctional aliphatic compounds with acrylic acids.

RELATED APPLICATIONS

Commonly assigned U.S. patent application Ser. No. 11/289,609, filed Nov. 30, 2005, to Peter G. Odell et al., describes a radiation curable phase change ink comprising an ink vehicle that includes a curable gellant comprised of a curable polyamide-epoxy acrylate component and a polyamide component, and at least one colorant.

Commonly assigned U.S. patent application Ser. No. 11/289,573, filed Nov. 30, 2005, to Gregory J. Kovacs et al., describes a pre-treatment composition comprising: one or more organic liquids chosen from the group consisting of $C_6$-$C_{30}$ linear alkanes, $C_6$-$C_{30}$ branched alkanes, $C_6$-$C_{30}$ linear alkenes and $C_6$-$C_{30}$ branched alkenes, and mixtures thereof; and one or more cross-linking initiators chosen from the group consisting of peroxy compounds and azo compounds.

Commonly assigned U.S. patent application Ser. No. 11/289,605, filed Nov. 30, 2005, to Gregory J. Kovacs et al., describes an ink-jettable overcoat composition for providing high-gloss, high-quality, and durable images, comprising: one or more organic liquids chosen from the group consisting of $C_6$-$C_{30}$ linear alkanes, $C_6$-$C_{30}$ branched alkanes, $C_6$-$C_{30}$ linear alkenes and $C_6$-$C_{30}$ branched alkenes, and mixtures thereof; and one or more film-forming materials.

Commonly assigned U.S. patent application Ser. No. 11/289,521, filed Nov. 30, 2005, to Jennifer L. Belelie et al., describes a composition, comprising: (a) curable monomer; (b) at least one photoinitiator that initiates polymerization of the curable monomer; and (c) phase change agent that provides the composition with an increase in viscosity of at least four orders of magnitude, from a first temperature, the first temperature being from 50° C. to 130° C., to a second temperature, the second temperature being from 0° C. to 70° C., wherein the second temperature is at least 10° C. below the first temperature.

Commonly assigned U.S. patent application Ser. No. 11/289,615, filed Nov. 30, 2005, to Jennifer L. Belelie et al., describes a radiation curable ink comprising curable monomer that is liquid at 25° C., curable wax, and colorant.

Commonly assigned U.S. patent application Ser. No. 11/289,552, filed Nov. 30, 2005, to Jennifer L. Belelie et al., describes an ink jettable overprint composition, comprising: at least one of a polymerizable monomer and/or a polymerizable oligomer; at least one photoinitiator; and at least one wax.

Commonly assigned U.S. patent application Ser. No. 11/289,620, filed Nov. 30, 2005, to Peter G. Odell et al., describes a phase change ink having a viscosity of from about 4 mPa·s to about 50 mPa·s at a first temperature and having a viscosity of from $10^4$ mPa·s to about $10^9$ mPa·s at a second temperature, the second temperature being below the first temperature by at least 10° C., but by no more than 50° C.

Commonly assigned U.S. patent application Ser. No. 11/289,375, filed Nov. 30, 2005, to Daryl W. Vanbesien et al., describes a toner composition comprising toner particles, the toner particles comprising: (i) polymer comprising photoinitiator and (ii) unsaturated curable resin.

Commonly assigned U.S. patent application Ser. No. 11/289,473, filed Nov. 30, 2005, to Rina Carlini et al., describes a radiation curable phase change ink comprising an ink vehicle that includes at least one gellant comprising a curable epoxy-polyamide composite gellant and at least one colorant.

Commonly assigned U.S. patent application Ser. No. 11/136,525, filed May 25, 2005, to Jennifer L. Belelie et al., describes a radiation curable phase change ink comprising an ink vehicle that includes at least one gellant comprising a curable epoxy-polyamide composite gellant and at least one colorant.

Commonly assigned U.S. patent application Ser. No. 11/451,342 entitled "Vehicles for Ink Compositions," filed concurrently with the instant application, to Peter G. Odell, describes an ink composition comprising a homogeneous ink vehicle that comprises one or more curable components, wherein the curable components are chosen from molecules including two reactive functional groups and one or more long aliphatic hydrocarbon chains.

Other curable inks that that are described to achieve more robust images following curing have also been described. Reference is made to the following patent properties: (1) Co-pending application Ser. No. 11/034,850 filed Jan. 14, 2005; (2) Co-pending application Ser. No. 11/034,856 filed Jan. 14, 2005; (3) Co-pending application Ser. No. 11/034,714 filed Jan. 14, 2005; (4) Co-pending application Ser. No. 11/018,378 filed Dec. 22, 2004; and (5) Co-pending application Ser. No. 11/034,866 filed Jan. 14, 2005.

The appropriate components and process aspects of each of the foregoing, such as the ink composition components and imaging processes, may be selected for the present disclosure in embodiments thereof. The entire disclosures of the above-mentioned applications are totally incorporated herein by reference.

REFERENCES

Song et al. (Shiyou Daxue Xeebao, Ziran Kexueban, 24(6), 49-51 (2000)) describes a synthetic route to a diacrylate that is useful in phase-change ink-jet ink compositions. The Song synthesis involves reacting a diol, with a 20% molar excess of acrylic acid in the presence of toluene sulfonic acid (1%) and hydroquinone (0.8%). Hydroquinone is included in the reaction mixture to prevent acrylate polymerization. The reaction is carried out at 120° C. for eight hours, and an azeotrope is employed to remove the by-product water. The excess acrylic acid is removed by distillation.

Lui et al. (J. Poly. Sci. Part A, 41, 4001-4006 (2003)) describes the esterification of the carboxylic acid of 2,2-bis(hydroxymethyl)proprionic acid followed by the reaction of the hydroxyl groups with a chloroformate.

Li et al. (Macromolecules, 37, 5190-5195 (2004)) describes the synthesis of a bisproprionate propionyl chloride from 2,2-bis(hydroxymethyl)propionic acid and the subsequent reaction of the acid chloride with a diol.

Ihre et al. (J. Am. Chem. Soc., 123(25) 5908-5917 (2001)) describes the protection of the hydroxyl groups of 2,2-bis (hydroxymethyl)propionic acid with benzaldehyde dimethyl acetol using gentle conditions. The propionic acid groups of the hydroxyl-protected compound then can be coupled with a diol, in the presence of N,N'-dicyclohexyl carbodiimide. After coupling, the hydroxyl groups can be de-protected using hydrogenation over palladium carbon catalyst.

Lu et al. (Polymer, 46, 9863-9870 (2005)) demonstrates the preferential reaction of isocyanates for the hydroxyl groups of 2,2-bis(hydroxyl-methyl)proprionic acid over the carboxylic acid group.

Guan et al. (J. Polym. Sci. Part A: Polym. Chem., 43, 1144-1149 (2005)) describes the protection of the carboxylic acid group 2,2-bis(hydroxyl-methyl)proprionic acid by forming a benzyl ester followed by reaction of the hydroxyl groups with an acid chloride and subsequent deprotection by hydrogenolysis.

The disclosures of each of the foregoing patents and publications are hereby incorporated by reference herein in their entireties. The appropriate components and process aspects of the each of the foregoing patents and publications may also be selected for the present compositions and processes in embodiments thereof.

BACKGROUND

Phase-change inks are desirable for ink-jet printers because they remain in a solid phase at room temperature during shipping, long-term storage, and the like. In addition, the problems associated with nozzle clogging as a result of ink evaporation with liquid ink-jet inks are largely eliminated, thereby improving the reliability of the ink-jet printing. Further, in phase-change ink-jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Phase-change or "hot-melt" inks typically used with ink-jet printers have a wax-based ink vehicle, e.g., a crystalline wax. Such solid ink-jet inks provide vivid color images. In typical systems, these crystalline-wax inks partially cool on an intermediate-transfer member and are then pressed into the image-receiving medium such as paper. Transfuse spreads the image droplet, providing a richer color and lower pile height. The low flow of the solid ink also prevents show-through on the paper.

However, the brittle waxes used in inks such as those described above do not provide robust images and are easily scratched. Low-viscosity inks, such as those curable by ultraviolet (UV) radiation, provide one printing option that is both jettable and curable to robust image on paper. These inks lack the thermally driven change in viscosity of hot-melt inks required to successfully transfuse the image as well as prevent image show-through on paper. In addition, UV-curable resin removes the requirement for a hard-wax ink vehicle. The resin can be cured to a tougher material than could ever be found with a wax. However, the transfuse drum makes use of the post-jetting solidification of the wax to preserve dot integrity while the image is built and transferred.

The majority of functionalized materials useful for UV curing are difunctional. Multifunctionality insures that the desired cross-linked network will be achieved. In the dominantly used class, acrylates, three major classes exist: polyethers, polyesters, and polyurethanes, all of which contain oxygen and/or nitrogen in the backbone. Only polyethers prepared from ethylene and propylene glycols have the ability to be of sufficiently low viscosity to be the major component of ink-jettable inks. There are very few long-chain acrylate-mono-functional hydrocarbon monomers and no commercial examples of difunctional acrylates with long hydrocarbon chains. Thus, there remains a need for processes for preparing difunctional acrylates having long hydrocarbon chains.

SUMMARY

The present disclosure addresses this and other needs, by providing processes for preparing difunctional acrylates having long hydrocarbon chains.

Exemplary methods include processes for preparing difunctional acrylate compounds that include long-chain hydrocarbon chains. Such methods include reacting $AB_2$ monomers with acryloyl halides, and then further reacting with aliphatic, long-chain, mono-functional aliphatic compounds to form long-chain diacrylates.

Exemplary methods also include processes for preparing difunctional diacrylate and compounds having long hydrocarbon chains by reacting difunctional aliphatic compounds with acrylic acid. The difunctional aliphatic compounds may be dimers, such as dimer diols or dimer amines.

These and other features and advantages of various exemplary embodiments of materials, devices, systems and/or methods are described in or are apparent from, the following detailed description.

EMBODIMENTS

This disclosure is not limited to particular embodiments described herein, and some components and processes may be varied by one of skill, based on this disclosure. The terminology used herein is for the purpose of describing particular embodiments only, and is not intended to be limiting.

In this specification and the claims that follow, singular forms such as "a," "an," and "the" include plural forms unless the content clearly dictates otherwise. In addition, reference may be made to a number of terms that shall be defined as follows:

The term "organic molecule" refers, for example, to any molecule that is made up predominantly of carbon and hydrogen, such as, for example, alkanes and arylamines. The term "heteroatom" refers, for example, to any atom other than carbon and hydrogen. Typical heteroatoms included in organic molecules include oxygen, nitrogen, sulfur and the like.

The term "aliphatic compound" refers, for example, to any molecule that is made up predominantly of straight-chain molecules.

The term "long-chain" refers, for example, to hydrocarbon chains in which n is a number of from about 8 to about 60, such as from about 20 to about 45 or from about 30 to about 40. The term "short-chain" refers, for example, to hydrocarbon chains in which n is a number of from about 1 to about 7, such as from about 2 to about 5 or from about 3 to about 4.

The term "alkyl" refers, for example, to a branched or unbranched saturated hydrocarbon group, derived from an alkane and having the general formula $C_nH_{2n+1}$, in which n is a number of 1 or more, such as of from about 1 to about 60. Exemplary alkyl groups include methyl, ethyl, n-propyl, isopropyl, n-butyl, isobutyl, tert-butyl, octyl, decyl, tetradecyl, hexadecyl, eicosyl, tetracosyl and the like. The term "lower alkyl" refers, for example, to an alkyl group of from about 1 to about 12 carbon atoms. "Substituted alkyl" refers, example, to an alkyl group in which at least one hydrogen atom, and optionally all hydrogen atoms, is replaced by a functional group.

The term "alkylene" refers, for example, to a branched or unbranched saturated hydrocarbon group of about 1 to about 40 carbon atoms and having two bonds to other portions of the molecule. Exemplary alkylene groups have the structure $—(CH_2)_a—$, in which a is an integer in a range of from about 1 to about 40.

The term "derivative" refers, for example, to compounds that are derived from another compound and maintain the same general structure as the compound from which they are derived. For example, saturated alcohols and saturated amines are derivatives of alkanes.

The term "functional group" refers, for example, to a group of atoms arranged in a way that determines the chemical properties of the group and the molecule to which it is attached. Examples of functional groups include halogen atoms, hydroxyl groups, carboxylic acid groups and the like.

The terms "halogen" or "halogen atom" refer, for example, to atoms of the elements fluorine (F), chlorine (Cl), bromine (Br), iodine (I) and astatine (At). The term "halo" refers, for example, to substitution of a halogen atom for a hydrogen atom in an organic compound. "Haloalkyl" refers, for example, to an alkyl moiety in which one or more of the hydrogen atoms has been replaced by a halogen atom. The term "lower haloalkyl" refers, for example, to an alkyl group of about 1 to about 6 carbon atoms in which at least one, and optionally all, of the hydrogen atoms has been replaced by a halogen atom. The term "perhalogenated" refers, for example, to a compound in which all of the hydrogen atoms have been replaced by halogen atoms, while the phrase "partially halogenated" refers, for example, to a compound in which less than all of the hydrogen atoms have been replaced by halogen atoms.

"Alcohol" refers, for example, to an alkyl moiety in which one or more of the hydrogen atoms has been replaced by an —OH group. The term "lower alcohol" refers, for example, to an alkyl group of about 1 to about 6 carbon atoms in which at least one, and optionally all, of the hydrogen atoms has been replaced by an —OH group. The term "primary alcohol" refers, for example to alcohols in which the —OH group is bonded to a terminal or chain-ending carbon atom, such as in methanol, ethanol, 1-propanol, 1-butanol, 1-hexanol and the like. The term "secondary alcohol" refers, for example to alcohols in which the —OH group is bonded to a carbon atom that is bonded to one hydrogen atom and to two other carbon atoms, such as in 2-propanol(isopropanol), 2-butanol, 2-hexanol and the like. The term "tertiary alcohol" refers, for example to alcohols in which the —OH group is bonded to a carbon atom that is bonded to three other carbon atoms, such as in methylpropanol (tert-butanol) and the like.

"Amine" refers, for example, to an alkyl moiety in which one or more of the hydrogen atoms has been replaced by an —$NH_2$ group. The term "lower amine" refers, for example, to an alkyl group of about 1 to about 6 carbon atoms in which at least one, and optionally all, of the hydrogen atoms has been replaced by an —$NH_2$ group.

"Carbonyl compound" refers, for example, to an organic compound containing a carbonyl group, C=O, such as, for example, aldehydes, which have the general formula RCOH; ketones, which have the general formula RCOR'; carboxylic acids, which have the general formula RCOOH; and esters, which have the general formula RCOOR'.

The term "ether" refers, for example, to an organic compound that contains one or more —O— groups in its molecule.

The term "epoxide" refers, for example, to an organic compound that contains one oxygen atom as part of a three-membered ring with carbon atoms. Epoxides are cyclic ether compounds. The terms "epoxy" and "epoxy group" refer, for example, to the three-membered ring containing one oxygen atom.

The term "acryloyl halide" refers, for example, to molecules of general formula X—$COCHCH_2$, in which X refers to, for example, a halide atom. The term "halide atom" refers, for example, to atoms chosen from fluorine, chlorine, bromine, iodine, and astatine.

The term "low molecular-weight alkyl acrylic ester" refers, for example, to acrylic esters having the general formula $CH_2CHCOOR$, in which R is chosen from $C_{1-22}$ alkyl groups such as methyl (—$CH_3$), ethyl (—$C_2H_5$), propyl (—$C_3H_7$) butyl (—$C_4H_9$), pentyl (—$C_5H_{11}$), hexyl (—$C_6H_{13}$), octyl (—$C_8H_{17}$), decyl (—$C_{10}H_{21}$), dodecyl (—$C_{12}H_{25}$), stearyl (—$C_{18}H_{37}$), and behenyl (—$C_{22}H_{45}$) alkyl groups and mixtures thereof.

The term "$AB_2$ monomer" refers, for example, to monomers that are aliphatic compounds having two different functional groups, A and B, in a ratio of one A group to two B groups. In these $AB_2$ monomers, the two functional groups A and B have different chemical reactivities, and one of the functional groups A and B includes one or more ethylenically unsaturated group.

The term "dimer" refers, for example, to compounds formed by the combination of two identical monomer molecules.

The term "reflux" refers, for example, to the process of boiling a liquid, condensing the vapor and returning the vapor to the original container. When a liquid is refluxed, the temperature of the boiling liquid remains constant. The term "boiling point" refers, for example, to the temperature at which the saturated vapor pressure of a liquid is equal to the external atmospheric pressure.

The terms "standard temperature" and "standard pressure" refer, for example, to the standard conditions used as a basis where properties vary with temperature and/or pressure. Standard temperature is 0° C.; standard pressure is 101,325 Pa or 760.0 mmHg. The term "room temperature" refers, for example, to temperatures in a range of from about 20° C. to about 25° C.

"Selective" or "selectively" refer, for example, to reactions in which the reaction occurs at only one reaction site of multiple possible reaction sites where such a reaction could theoretically occur. For example, a selective hydrogenation reaction of a propenoic acid compound may add hydrogen across only the carbon-carbon double bond, and not across the carbon-oxygen double bond, to form a propanoic acid compound.

"Optional" or "optionally" refer, for example, to instances in which subsequently described circumstance may or may not occur, and include instances in which the circumstance occurs and instances in which the circumstance does not occur.

The terms "one or more" and "at least one" refer, for example, to instances in which one of the subsequently described circumstances occurs, and to instances in which more than one of the subsequently described circumstances occurs.

In ink-jet systems using solid or phase-change ink compositions, post-jetting solidification of a low-temperature melting component, such as wax, is desired to preserve the integrity of jetted-ink droplets while the image is built and transferred to the recording substrate. In ink-jet systems that use phase-change ink that is curable, it is preferable to use long hydrocarbon chains that have acrylate functionality in the ink vehicle. Provided herein are methods for producing long-chain hydrocarbons with acrylate functionality.

In embodiments, a difference in reactivity between A groups and B groups allows synthesis of difunctional molecules with long wax-like hydrocarbon chains. Such $AB_2$ diacrylates can be used as a major component of solid or "phase-change" ink jet ink compositions, for example when combined with mono-functional acrylates, vinyl ethers and/or non-functional waxes. The long chain length of the $AB_2$ diacrylates of embodiments allows wax-like behavior and compatibility with polyethylene waxes.

Long-Chain $AB_2$ Diacrylate Hydrocarbon Compounds

In exemplary methods, difunctional acrylate compounds including long hydrocarbon chains may be prepared by reacting $AB_2$ monomers with acryloyl halides, and then further reacting with aliphatic long-chain, mono-functional aliphatic compounds to form long-chain $AB_2$ diacrylate hydrocarbon compounds. Some exemplary methods include optionally protecting an A group of an $AB_2$ monomer with a suitable first selective protecting group; reacting the B groups of the $AB_2$ monomer with an acryloyl halide to form an $AB_2$ diacrylate; optionally removing the first selective protecting group from the A group and/or optionally protecting acrylate groups of the $AB_2$ diacrylate with a suitable second selective protecting group; further reacting the $AB_2$ diacrylate with an aliphatic long-chain, mono-functional aliphatic compound to form a long-chain $AB_2$ diacrylate.

In embodiments, A groups of the $AB_2$ monomers may more readily undergo nucleophilic substitution than B groups, and this may be accomplished by selectively protecting A groups using any suitable protecting group known in the art, such as those disclosed in Green and Wuts, "Protective Groups in Organic Synthesis," or later developed. In addition, B groups may be convertible to acrylate groups. Otherwise, neither A groups nor B groups are particularly limited.

Suitable functional groups useful as A groups in embodiments include carboxylic acid groups, benzyl alcohol groups and the like. Suitable functional groups useful as B groups in embodiments may be hydroxyl groups, thiol groups, amine groups, amide groups, imide groups, phenol groups, and mixtures thereof. Exemplary $AB_2$ monomers include, for example, bishydroxy alkyl carboxylic acids ($AB_2$ monomers in which A is carboxylic acid and B is hydroxyl), 2,2-bis(hydroxymethyl)butyric acid, N,N-bis(hydroxyethyl)glycine, 2,5-dihydroxybenzyl alcohol, 3,5-bis(4-aminophenoxy)benzoic acid, and the like. Exemplary $AB_2$ monomers also include those disclosed in Jikei et al. (Macromolecules, 33, 6228-6234 (2000)).

In embodiments, the process may begin by optionally protecting the B group of an $AB_2$ monomer with a suitable first selective protecting group. Suitable protecting groups and methods for protecting the B group will be known to those of skill in the art, based on the B group. Examples of protecting groups that may be used in some embodiments as the first selective protecting group include benzaldehyde dimethyl acetal, benzyl ester and the like.

Exemplary methods include reacting the B groups of the $AB_2$ monomer with an acryloyl halide to form an $AB_2$ diacrylate. Examplary reactions may be, for example, carried out with acryloyl chloride in methylene chloride at 0° C. with pyridine or triethylamine used as the base to remove the chloride by-product. Equimolar amounts or a slight excess of acryloyl chloride may be used relative to the B hydroxyl groups. Equally effective would be B groups consisting of primary amines.

In embodiments, the acryloyl halide may be chosen from acryloyl fluoride, acryloyl chloride, acryloyl bromide, and acryloyl iodide, and mixtures thereof. In particular embodiments, the acryloyl halide is acryloyl chloride.

Exemplary methods may include optionally protecting the B groups first. Methods for protecting groups such as hydroxyls will be known to those of skill in the art. An examplary method for $AB_2$ monomers such as 2,2-bis(hydroxyl-methyl)proprionic acid is the use of benzaldehyde dimethyl acetal catalyzed by a sulfonic acid such as p-toluene sulfonic acid in acetone at room temperature to form benzylidene-2,2-bis(oxymethyl)proprionic acid. This protected $AB_2$ monomer may be subsequently coupled with an aliphatic alcohol. Suitable aliphatic alcohols include stearyl alcohol; 1-docosanol; hydroxyl-terminated polyethylene waxes, such as mixtures of carbon chains with the structure $CH_3$—$(CH_2)_n$—$CH_2OH$, where there is a mixture of chain lengths, n, having an average chain length, in some embodiments, in the range of about 12 to about 100; and linear low molecular weight polyethylenes that have an average chain length similar to that of the described hydroxyl-terminated polhyethylene waxes. Suitable examples of such waxes include, but are not limited to, UNILIN 350, UNILIN 425, UNILIN 550 and UNILIN 700 with $M_n$ approximately equal to 375, 460, 550 and 700 g/mol, respectively. All of these waxes are commercially available from Baker-Petrolite. Guerbet alcohols, characterized as 2,2-dialkyl-1-ethanols, are also suitable compounds. In particular embodiments, the Guerbet alcohols may be chosen from Guerbet alcohols containing 16 to 36 carbon atoms; many such Guerbet alcohols are commercially available from Jarchem Industries Inc., Newark, N.J.

The acid group of the $AB_2$ monomer may be esterified by the alcohol using p-toluenesulfonic acid in refluxing toluene. Following the reaction of the aliphatic alcohol with the protected $AB_2$ monomer, the protecting groups may be removed in methylene chloride using a palladium carbon catalyst under hydrogen gas. Once deprotected, the final product diacrylate aliphatic ester may be made using acryloyl chloride in methylene chloride with pyridine or triethylamine to remove the chloride ion.

Suitable mono-substituted aliphatic compounds have, in embodiments, the general formula $C_nH_{2n}W$ in which W is a functional group selected from the group consisting of hydroxyl groups, carboxylic acid groups, thiol groups, amine groups, amide groups, and mixtures thereof, and in which n is in a range of from about 8 to about 60, such as from 10 to about 40 or from about 15 to about 35.

Exemplary mono-substituted, long-chain aliphatic compounds may include stearyl alcohol ($C_{18}H_{36}OH$) and cetyl alcohol ($C_{16}H_{32}OH$), for example, as well as hydroxyl-terminated waxes, such as UNILIN hydroxyl-terminated waxes (commercially available from Baker-Petrolite); and hydroxyl-terminated branched hydrocarbons, such as Guerbet alcohols, including JARCOL-16 and ISOFOL-36 (available from Condea).

Reacting the $AB_2$ diol with a mono-substituted, long-chain aliphatic acid to form a long-chain $AB_2$ diacrylate may be conducted by any suitable method, including, for example, condensation. The resultant long-chain $AB_2$ diacrylates may optionally be purified by any suitable known or later developed method.

Diacryl-Functional Dimer Compounds

In exemplary methods, dimer-difunctional compounds may be prepared by reacting difunctional aliphatic compounds with acrylate-functional compounds in the presence of a diimide. Like the $AB_2$ diacrylates of embodiments described above, dimer difunctional compounds of embodiments can be used as a major component of solid or "phase-change" ink-jet ink compositions.

The difunctional aliphatic compounds may be dimers, such as dimer diols or dimer amines. Difunctional aliphatic compounds of embodiments are branched aliphatic compounds that include a total of from about 12 to about 80 carbon atoms, such as from about 20 to about 60 carbon atoms, or from about 35 to about 45 carbon atoms. The difunctional aliphatic compounds, in embodiments, may include a number of carbon atoms "m" arranged as one hydrocarbon chain of about m/2 carbon atoms with two side chains having a total of about m/2 carbon atoms. In particular embodiments, the difunctional aliphatic compound may be arranged as one hydrocarbon chain of about m/2 carbon atoms and two side chains having a total of about m/4 carbon atoms in each side chain. For example, the difunctional aliphatic compounds of particular embodiments may be chosen from PRIPOL 2030 or PRIPOL 2033, which is a $C_{36}$ dimer diol mixture including isomers of formula (I):

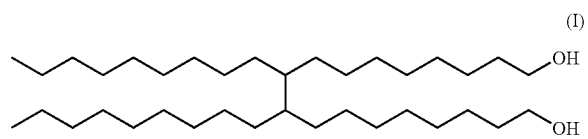

(I)

as well as other branched isomers, which may include unsaturations and cyclic groups, available from Uniqema, New Castle, Del. Dimer diols may be derived from dimer acids, and additional information on $C_{36}$ dimer acids of this type can be found, for example, in "Dimer Acids," *Kirk-Othmer Encyclopedia of Chemical Technology*, Vol. 8, pp. 223-237 ($4^{th}$ Ed. 1992).

Examples of dimer diols, dimer diamines, and dimer diacids that may be used in accordance with embodiments include, for example, the aforementioned PRIPOL 2030 and PRIPOL 2033, Spezial C36-2 Dimer Diol (commercially available from Cognis Corporation).

The acrylate-functional compounds of embodiments may be chosen from acrylates, methacrylates, acrylic acids, methacrylic acids, low molecular-weight alkyl acrylic esters, and mixtures thereof. In embodiments, the acrylate-functional compound may be chosen from acrylic acid methyl acrylic ester, ethyl acrylic ester, propyl acrylic ester and butyl acrylic ester, and mixtures thereof.

In embodiments, a difunctional aliphatic compound is reacted with acrylic acid (from about 5° C. to about 90° C.) to yield the dimer diacrylate. The difunctional aliphatic compound may be present in amounts that are approximately the same as the amounts of acrylic acid present. That is, the acrylic acid and difunctional aliphatic compound may be present in approximately equimolar amounts, and in some embodiments, a slight excess of acrylic acid may be present. The reaction may be conducted in the presence of a solvent, such as methylene chloride.

The product of exemplary methods may be purified by any suitable known or later developed method to produce dimer diacrylates.

Specific examples are described in detail below. These examples are intended to be illustrative, and the materials, conditions, and process parameters set forth in these exemplary embodiments are not limiting. All parts and percentages are by weight unless otherwise indicated.

EXAMPLES

Example I

AB$_2$ Diacrylate Synthesis

In a 100-mL round-bottomed flask, 6 grams of 2,2-bis(hydroxymethyl)propionic acid (45 mmoles) are combined with 9.0 grams of acryloyl chloride (100 mmoles) and 15 grams of triethylamine in 60 grams methylene chloride. The mixture is stirred at 22° C. for 3 hours. The methylene chloride solution is washed three times with deionized water and then dried over magnesium sulphate and filtered. To the washed reaction mixture, 9.3 grams of stearyl alcohol (1-octadecanol), and 0.5 grams of 4-dimethylaminopyridine are added. The stirred solution is cooled, and 10.8 grams of 1,3-dicyclohexylcarbodiimide added over the course of 30 minutes. The resulting mixture is allowed to warm to room temperature over four hours. The product is isolated by washing with deionized water three times, followed by one wash with saturated sodium chloride solution. The organic layer is then dried over magnesium sulfate and the solvent removed by rotary evaporation. This reaction is illustrated below. Both steps of the reaction are monitored by $H^1$ NMR. The product is 2,2-bis(acryloylmethyl)propionic stearyl ester.

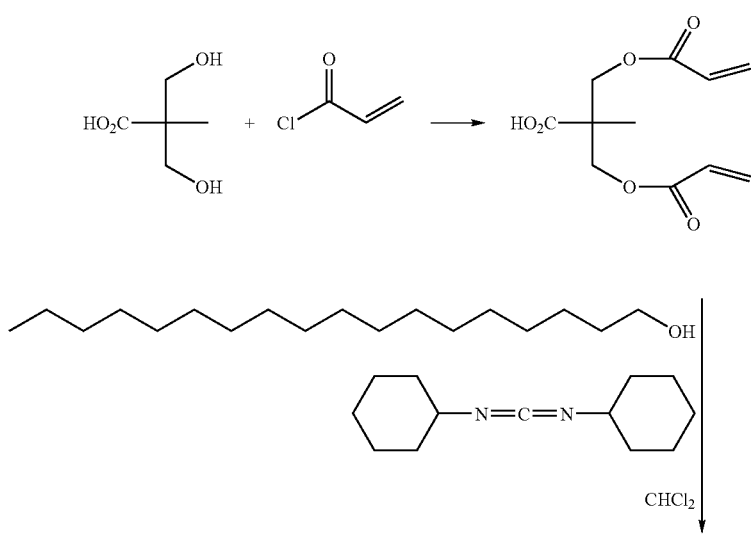

-continued

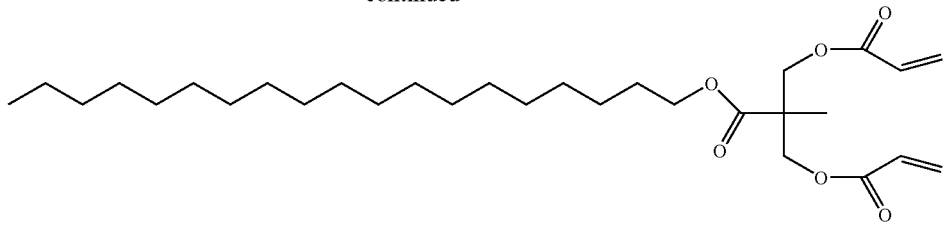

Example II

AB$_2$ Diacrylate Synthesis

Benzylidene-2,2-bis(oxymethyl)propionic acid is prepared by the method of Ihre et al. (J. Am. Chem. Soc., 123(25) 5908-5917 (2001)). In a 250-mL round-bottomed flask equipped with a stirrer and Dean-Stark apparatus, 15 grams of benzylidene-2,2-bis(oxymethyl)propionic acid (67 mmoles) are combined with 18.2 grams of 1-octadecanol (67 mmoles) and 1.8 grams of p-toluene sulfonic acid in 120 grams of toluene. The mixture is heated to reflux and maintained at reflux until water ceases to collect in the Dean-Stark apparatus. The toluene solution is cooled, and the cooled toluene solution is washed three times with deionized water. Toluene is then removed from the product (approximately 32 grams), and the product is redissolved in 180 mL of methylene chloride. The protecting groups are removed using 0.6 grams of palladium on 5 wt % carbon catalyst under H$_2$ at room temperature for 16 hours. Deionized water (0.5 mL) is added to the solution of deprotected product, 2,2-bis(hydroxymethyl) propionic stearyl ester, and then the mixture is filtered through phase separating filter paper.

The solution of 2,2-bis(hydroxymethyl)propionic stearyl ester in methylene chloride is transferred to a 500-mL round-bottomed flask, and 12.7 grams of acryloyl chloride (140 mmoles) and 21.2 grams of triethylamine are gradually added to the flask from separate addition funnels. The mixture is stirred at 22° C. for 3 hours. The methylene chloride solution is washed three times with deionized water. The organic layer is then dried over magnesium sulfate, filtered and the solvent removed by rotary evaporation. Both steps of the reaction are monitored by H$^1$ NMR. The product is 2,2-bis(acryloylmethyl)propionic stearyl ester.

Example III

Diacrylate Synthesis from C$_{36}$ Dimer Diol

In a 100-mL jacketed reaction flask, 26.9 grams of a commercially available C$_{36}$ dimer diol, PRIPOL 2033 (available from Uniqema) were combined with 9.0 grams of acrylic acid and 0.9 grams of 4-dimethylaminopyridine in 75 grams of methylene chloride. To this mixture, 30.9 grams of 1,3-dicyclohexylcarbdiimide was added over the course of 30 minutes while the temperature was maintained at 5° C. The temperature was then raised to 30° C. for a further 5 hours. The product was isolated by washing with deionized water three times, followed by one wash with saturated sodium chloride solution. The organic layer was then dried over magnesium sulfate, and the solvent was removed by rotary evaporation. The extent of reaction was followed by H$^1$ NMR by comparing the product peak at 4.2 ppm (methylene protons adjacent to an ester oxygen) to the starting material at 3.8 ppm (methylene protons adjacent to an alcohol). The yield of this reaction was 73%.

Example IV

Diacrylate Synthesis from C$_{36}$ Dimer Diol

A total weight of 87.7 grams of partially esterified reaction products from Example II and similar reactions were combined in a 2-L jacketed reaction flask, with 14.4 grams of acrylic acid and 5.6 grams of 4-dimethylaminopyridine in 280 grams of toluene. To this mixture, 45.4 grams of 1,3-dicyclohexylcarbdiimide was added over the course of 60 minutes while the temperature was maintained at 5° C. The temperature was then raised to 90° C. for a further 4.5 hours. The product was isolated by the same procedure as Example II. The isolated material consisted of white crystals and a yellow oil. H$^1$ NMR revealed that the oil was the desired product. This reaction is illustrated below.

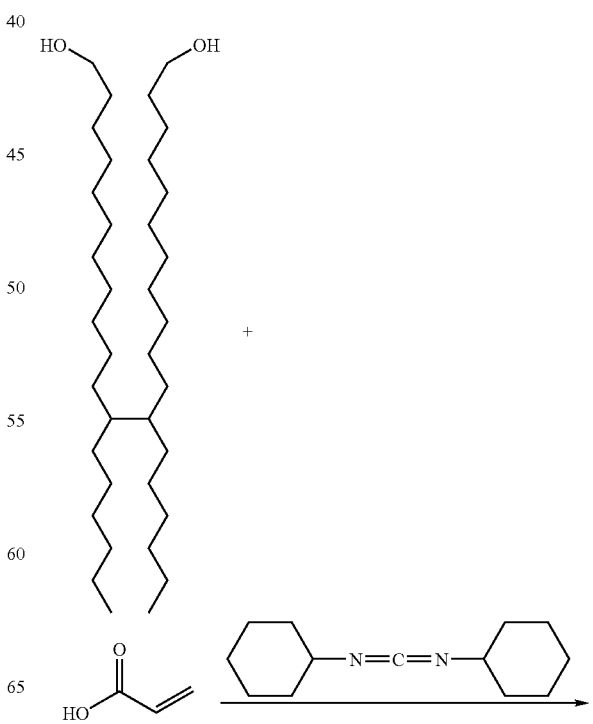

-continued

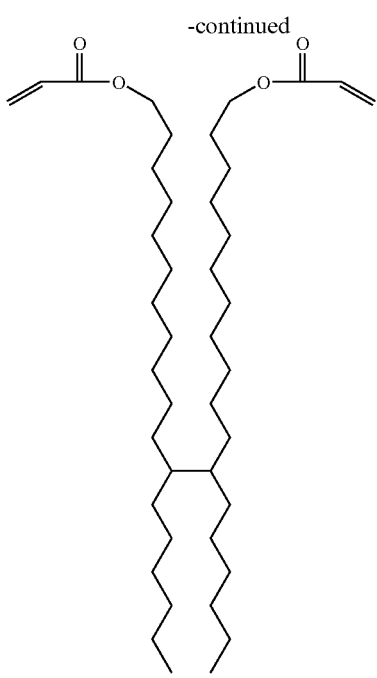 + 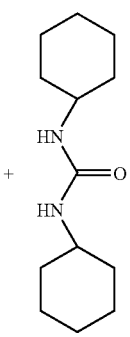

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A process for preparing long-chain $AB_2$ diacrylate compounds, comprising:
   reacting an $AB_2$ monomer and an acryloyl halide to form an $AB_2$ diacrylate; and
   reacting the $AB_2$ diacrylate and a long-chain, mono-functional aliphatic compound to form a long-chain $AB_2$ diacrylate-compound.

2. The process according to claim 1, wherein the $AB_2$ monomer comprises an aliphatic compound containing one functional group A and two functional groups B; wherein
   the functional group A is chosen from the group consisting of carboxylic acid groups and benzyl alcohol groups;
   the functional groups B are the same and are chosen from the group consisting of hydroxyl groups, thiol groups, amine groups, amide groups, and phenol groups;
   the functional group A is different from the functional groups B; and
   the aliphatic compound is a hydrocarbon containing from about one to about seven carbon atoms.

3. The process according to claim 1, wherein the $AB_2$ monomer is chosen from the group consisting of bishydroxy alkyl carboxylic acids.

4. The process according to claim 3, wherein the $AB_2$ monomer is chosen from the group consisting of bishydroxy propyl carboxylic acids, bishydroxy butyl carboxylic acids, bishydroxy pentyl carboxylic acids, bishydroxy hexyl carboxylic acids, bishydroxy heptyl carboxylic acids, and mixtures thereof.

5. The process according to claim 1, wherein the acryloyl halide is chosen from the group consisting of acryloyl fluoride, acryloyl chloride, acryloyl bromide, acryloyl iodide, and mixtures thereof.

6. The process according to claim 1, wherein the long-chain, mono-functional aliphatic compound is chosen from aliphatic alcohols, aliphatic amines, aliphatic thiols, aliphatic amides, and mixtures thereof.

7. The process according to claim 1, wherein the long-chain, mono-functional aliphatic compound is chosen from stearyl alcohol, cetyl alcohol, hydroxyl terminated waxes, hydroxyl terminated branched hydrocarbons, and mixtures thereof.

8. The process according to claim 1, wherein the long-chain, mono-functional aliphatic compound contains from about 8 to about 60 carbon atoms in its hydrocarbon chain.

9. The process according to claim 6, wherein the long-chain, mono-functional aliphatic compound contains from about 10 to about 40 carbon atoms in its hydrocarbon chain.

10. The process according to claim 6, wherein the long-chain, mono-functional aliphatic compound contains from about 15 to about 35 carbon atoms in its hydrocarbon chain.

11. A process for preparing diacryl-functional compounds, comprising
    reacting a difunctional aliphatic compound with an acrylate-functional compound in the presence of a diimide.

12. The process according to claim 11, wherein the difunctional aliphatic compound is a difunctional dimer.

13. The process according to claim 11, wherein the difunctional aliphatic compound is a dimer chosen from dimer diols, dimer diamines, dimer dithiols, and mixtures thereof.

14. The process according to claim 11, wherein the difunctional aliphatic compound contains a total of from about 12 to about 80 carbon atoms.

15. The process according to claim 14, wherein the difunctional aliphatic compound contains a total of from about 20 to about 60 carbon atoms.

16. The process according to claim 14, wherein the difunctional aliphatic compound contains a total of from about 35 to about 45 carbon atoms.

17. The process according to claim 11, wherein the difunctional aliphatic compound is a branched hydrocarbon.

18. The process according to claim 11, wherein the difunctional aliphatic compound contains terminal functional groups.

19. The process according to claim 11, wherein the acrylate-functional compound is chosen from the group consisting of acrylic acid ester, methyl acrylic ester, ethyl acrylic ester, propyl acrylic ester, butyl acrylic ester, methacrylic acid ester, methyl methacrylic ester, ethyl methacrylic ester, propyl methacrylic ester, and butyl methacrylic ester and mixtures thereof.

20. The process according to claim 11, wherein reacting the difunctional aliphatic compound and the acrylate-functional compound further comprises reacting the difunctional aliphatic compound and the acrylate-functional compound in methylene chloride.

21. The process according to claim 11, wherein reacting the difunctional aliphatic compound and the acrylate-functional compound further comprises reacting the difunctional aliphatic compound and the acrylate-functional compound at room temperature.

* * * * *